US009936990B2

(12) United States Patent
Bourda et al.

(10) Patent No.: US 9,936,990 B2
(45) Date of Patent: Apr. 10, 2018

(54) BONE PEG HAVING IMPROVED EXTRACTION

(71) Applicant: Biomet C.V., Gibraltar (GI)

(72) Inventors: Marcus Bourda, Miami, FL (US);
Edward Mebarak, Miami, FL (US);
Victor Alvarez, Miami, FL (US);
Cesare Cavallazzi, Miami, FL (US)

(73) Assignee: Biomet C.V., Warsaw, IN (US)

( * ) Notice: Subject to any disclaimer, the term of this patent is extended or adjusted under 35 U.S.C. 154(b) by 473 days.

(21) Appl. No.: 14/623,857

(22) Filed: Feb. 17, 2015

(65) Prior Publication Data

US 2016/0235452 A1    Aug. 18, 2016

(51) Int. Cl.
| | | |
|---|---|---|
| *A61B 17/88* | (2006.01) | |
| *A61B 17/80* | (2006.01) | |
| *A61B 17/86* | (2006.01) | |

(52) U.S. Cl.
CPC ...... *A61B 17/8057* (2013.01); *A61B 17/8061* (2013.01); *A61B 17/863* (2013.01); *A61B 17/8615* (2013.01); *A61B 17/8635* (2013.01)

(58) Field of Classification Search
None
See application file for complete search history.

(56) References Cited

U.S. PATENT DOCUMENTS

| | | |
|---|---|---|
| 5,375,956 A | 12/1994 | Pennig |
| 8,257,405 B2 | 9/2012 | Haidukewych et al. |
| 2011/0118795 A1 | 5/2011 | Hashmi et al. |
| 2013/0096631 A1 | 4/2013 | Leung et al. |
| 2014/0031879 A1 | 1/2014 | Sixto, Jr. et al. |
| 2014/0228894 A1 | 8/2014 | Pacheco et al. |
| 2014/0257413 A1* | 9/2014 | Appenzeller ........ A61B 17/863 606/316 |

(Continued)

FOREIGN PATENT DOCUMENTS

| | | |
|---|---|---|
| WO | WO-2008129401 A1 | 10/2008 |
| WO | WO-2009058969 A1 | 5/2009 |

(Continued)

OTHER PUBLICATIONS

"International Application Serial No. PCT/US2016/018068, International Search Report dated Apr. 25, 2016", 7 pgs.

(Continued)

*Primary Examiner* — Sameh Boles
(74) *Attorney, Agent, or Firm* — Schwegman Lundberg & Woessner, P.A.

(57) ABSTRACT

A bone peg configured for cooperation with a threaded aperture on a bone plate for use in stabilizing a fracture of a bone can include a head portion and a shaft portion. The head portion can have a head threaded portion that incorporates head threads having a first pitch. The shaft portion can extend from the head portion to a distal end of the bone peg. The shaft portion can include (i) a shaft threaded portion that incorporates shaft threads having a second pitch, (ii) a first unthreaded portion and (iii) a second unthreaded portion. The shaft threaded portion is disposed intermediate the first and second unthreaded portions. The first unthreaded portion axially offsets the head threaded portion from the shaft threaded portion.

14 Claims, 4 Drawing Sheets

(56) References Cited

U.S. PATENT DOCUMENTS

2015/0088136 A1* 3/2015 Kotuljac ............ A61B 17/7291
606/64

FOREIGN PATENT DOCUMENTS

| WO | WO-2013131974 A1 | 9/2013 |
| WO | WO-2016133901 A1 | 8/2016 |

OTHER PUBLICATIONS

"International Application Serial No. PCT/US2016/018068, Written Opinion dated Apr. 25, 2016", 9 pgs.
"International Application Serial No. PCT/US2016/018068, International Preliminary Report on Patentability dated Aug. 31, 2017", 11 pgs.

* cited by examiner

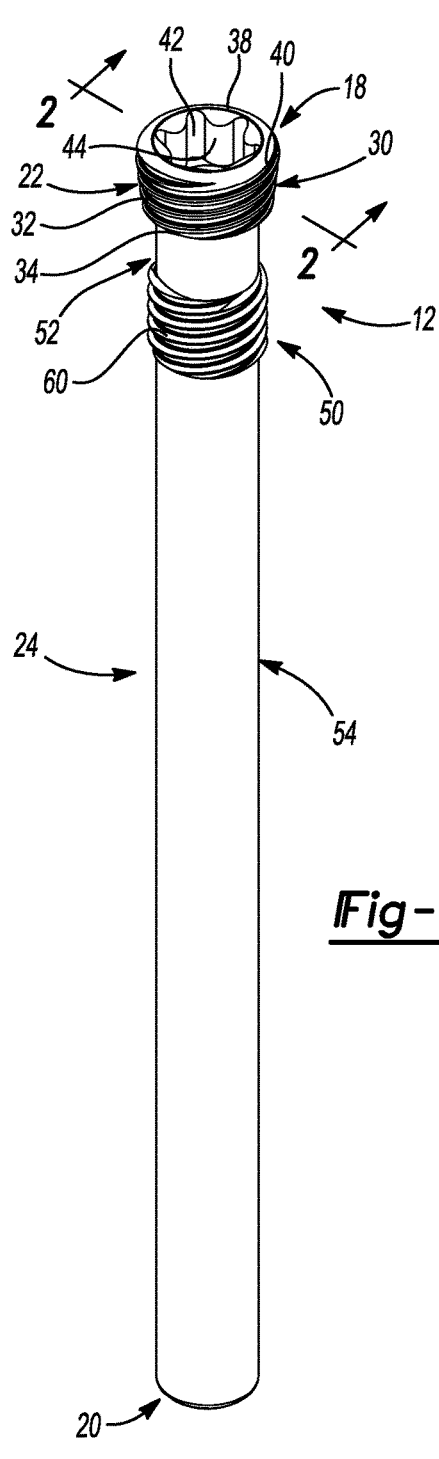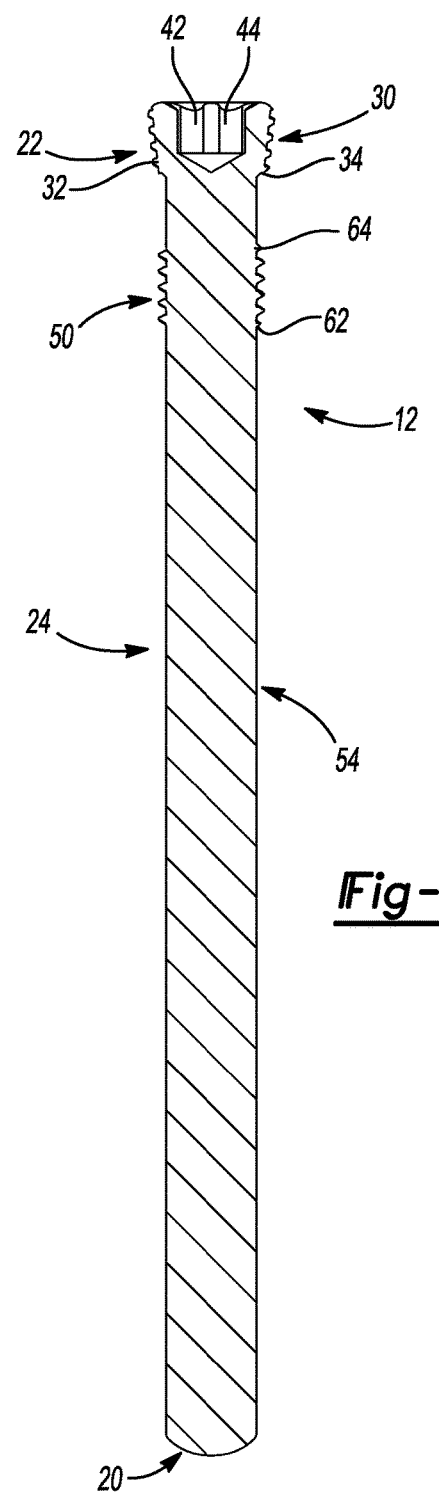

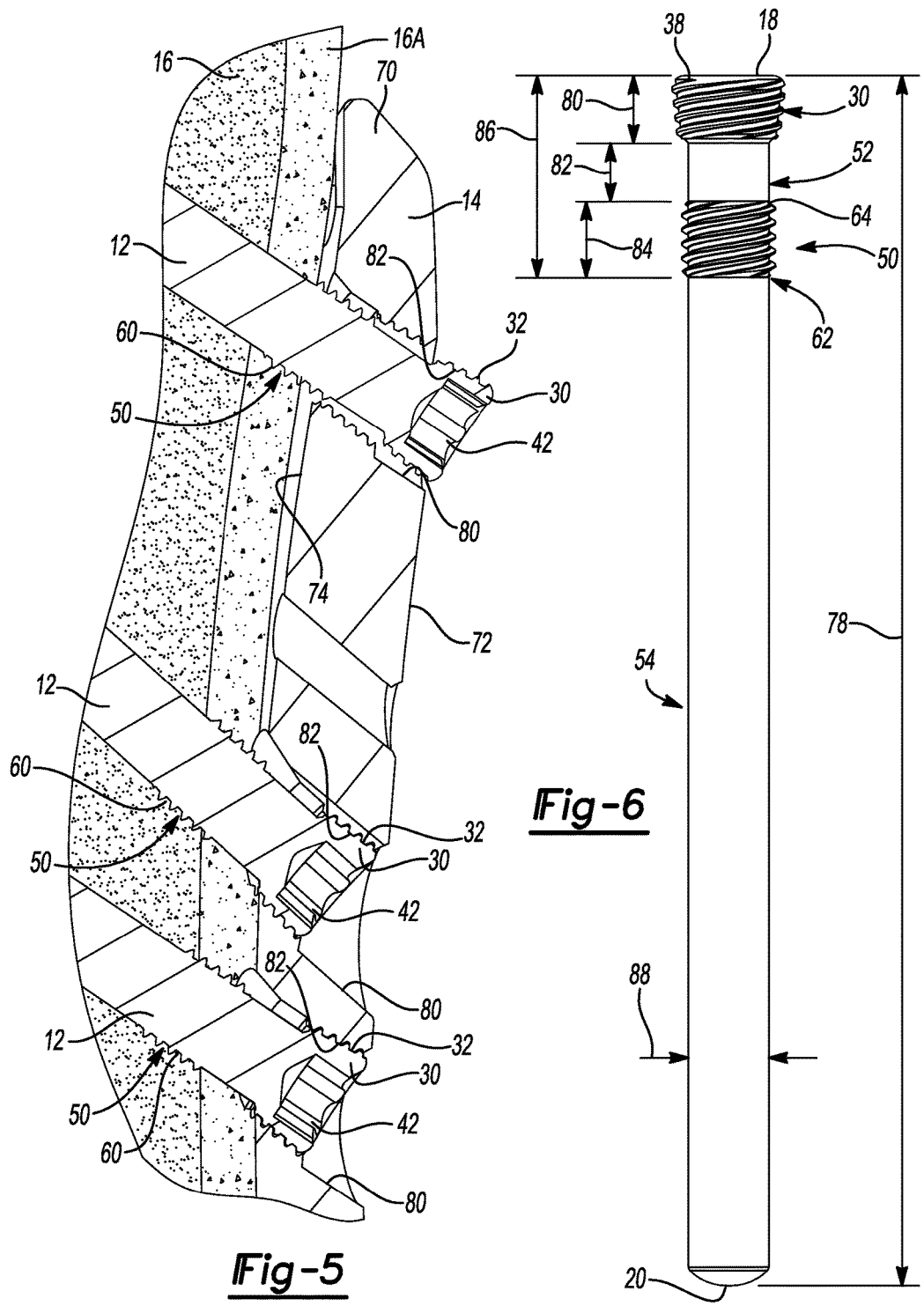

BONE PEG HAVING IMPROVED EXTRACTION

FIELD

The present disclosure relates generally to bone plating systems and, more particularly, to fixation devices and techniques for fixing a bone plate relative to bone with a bone peg having a thread configuration that facilitates improved removal of the bone peg from the bone.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In some instances it may be desirable to fix a bone plate to a proximal humerus such as to stabilize a fracture. The proximal humerus generally lacks typical bone density and has a sponge-like quality. In this regard, it is typical to use smooth pegs in combination with the bone plate to provide subchondral support to compensate for the insufficient cancellous material. Furthermore, such pegs are usually driven into the bone at divergent angles to prevent migration of the bone and plate once all the pegs have been implanted. In some instances the pegs may require removal due to improper peg measurement or surgical revision of the implant. Many times it is difficult to withdraw the peg from the bone and the head of the peg often stays submerged within the hole of the plate. A need exists in the art for a peg that allows for easier withdrawal from the bone and plate.

SUMMARY

This section provides a general summary of the disclosure, and is not a comprehensive disclosure of its full scope or all of its features.

A bone peg configured for cooperation with a threaded aperture on a bone plate for use in stabilizing a fracture of a bone can include a head portion and a shaft portion. The head portion can have a head threaded portion that incorporates head threads having a first pitch. The shaft portion can extend from the head portion to a distal end of the bone peg. The shaft portion can include (i) a shaft threaded portion that incorporates shaft threads having a second pitch, (ii) a first unthreaded portion and (iii) a second unthreaded portion. The shaft threaded portion is disposed intermediate the first and second unthreaded portions. The first unthreaded portion axially offsets the head threaded portion from the shaft threaded portion. The first and second pitches can be equivalent whereby the head threaded portion and the shaft threaded portion threadably advance along the threaded aperture of the bone plate and the bone, respectively in a synchronized manner.

According to additional features, the head threads define a first thread start and the shaft threads define a second thread start. The second thread start can be configured to initially mate with the bone at a first time. The first thread start can be configured to initially mate with the threaded aperture on the bone plate at a second time. The first time can occur before the second time when advancing the bone peg through the bone plate and into the bone. The shaft threads can maintain contact with the bone subsequent to the head threads clearing the threaded aperture of the bone plate during withdrawal of the bone peg from the bone.

According to additional features, the head portion tapers from an upper peripheral rim toward the shaft portion. The head portion can further include a tool engaging feature. The tool engaging feature can comprise a driver engagement socket. The head threads can be triple lead. The shaft threads can be triple lead. The head threaded portion can extend a first axial distance along the shaft portion. The first unthreaded shaft portion can extend a second axial distance along the shaft portion. The first and second axial distances are substantially equivalent. The first and second axial distances can be distinct by between 10 percent and 20 percent. The shaft threaded portion can extend a third axial distance along the shaft portion. The third axial distance can be between 15 percent and 25 percent longer than the first axial distance.

A bone plating system configured for stabilizing a fracture of a bone and constructed in accordance to one example of the present disclosure includes a bone peg and a bone plate. The bone peg can include a head portion and a shaft portion. The head portion can have a head threaded portion that incorporates head threads having a first pitch. The shaft portion can extend from the head portion to a distal end of the bone peg. The shaft portion can include (i) a shaft threaded portion that incorporates shaft threads having a second pitch, (ii) a first unthreaded portion and (iii) a second unthreaded portion. The shaft threaded portion is disposed intermediate the first and second unthreaded portions. The first unthreaded portion can axially offset the head threaded portion from the shaft threaded portion. The bone plate can include a plate body, a hole and a plate threaded portion. The plate body can have an upper surface and a lower surface. The hole can be defined through the plate body from the upper surface to the lower surface. The plate threaded portion can be defined by the plate body at the hole. The first and second pitches are equivalent whereby the head threaded portion and the shaft threaded portion threadably advance along the plate threaded portion of the bone plate and the bone, respectively in a synchronized manner.

According to other features, the head threads define a first thread start and the shaft threads define a second thread start. The second thread start can be configured to initially mate with the bone at a first time. The first thread start can be configured to initially mate with the threaded aperture on the bone plate at a second time. The first time can occur before the second time when advancing the bone peg through the bone plate and into the bone. The shaft threads can maintain contact with the bone subsequent to the head threads clearing the threaded aperture of the bone plate during withdrawal of the bone peg from the bone.

According to still additional features, the head portion tapers from an upper peripheral rim toward the shaft portion. The head portion can further include a tool engaging feature. The tool engaging feature can comprise a driver engagement socket. The head threads can be triple lead. The shaft threads can be triple lead. The head threaded portion can extend a first axial distance along the shaft portion. The first unthreaded shaft portion can extend a second axial distance along the shaft portion. The first and second axial distances are substantially equivalent. The first and second axial distances can be distinct by between 10 percent and 20 percent. The shaft threaded portion can extend a third axial distance along the shaft portion. The third axial distance can be between 15 percent and 25 percent longer than the first axial distance.

A method of stabilizing a fracture of a bone using a bone plate and a bone peg can include engaging a bone peg that extends through a threaded aperture in the bone plate. The bone peg includes (A) a head portion having head threads that define a first thread start, and (B) a shaft portion having (i) a shaft threaded portion that incorporates shaft threads having a second thread start, (ii) a first unthreaded portion and (iii) a second unthreaded portion. The shaft threaded portion is disposed intermediate the first and second unthreaded portions. The first unthreaded portion axially offsets the head threaded portion from the shaft threaded portion. The bone peg is withdrawn from the bone wherein the shaft threads maintain contact with the bone subsequent to the head threads clearing the threaded aperture of the bone plate.

According to other features, engaging the bone peg can further include engaging a tool engaging feature configured on the head portion. Prior to withdrawing the bone peg, the bone peg is advanced through the threaded aperture of the bone plate and into the bone. Advancing comprises advancing the bone peg into the bone wherein the second thread start initially mates with the bone at a first time. The bone peg is further advanced into the bone. The second thread start initially mates with a threaded aperture on the bone plate subsequent to the first time.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 1 is a front perspective view of a bone peg constructed in accordance with various aspects of the present disclosure;

FIG. 2 is a cross-sectional view of the bone peg taken along lines 2-2 of FIG. 1;

FIG. 5 is a detailed medial perspective view of the bone plate system of FIG. 4; and FIG. 6 is a side view of the bone peg of FIG. 1.

DETAILED DESCRIPTION

The following description is merely exemplary in nature and is not intended to limit the present disclosure, its application, or uses. Examples are provided so that this disclosure will be thorough, and will fully convey the scope to those who are skilled in the art. Numerous specific details are set forth such as examples of specific components, devices, systems and/or methods, to provide a thorough understanding of the present disclosure. It will be apparent to those skilled in the art that specific details need not be employed, that examples shown herein may be embodied in many different forms and that neither should be construed to limit the scope of the disclosure.

The present teachings provide a bone peg and related bone plate system and methods for using the same to facilitate bone fixation and healing. The particular examples discussed herein relate to fixation or stabilization of a fracture on a distal humerus however they are not so limited. In this regard, the present teachings may be applicable to fixation of any bone or bones. In an exemplary aspect, the bone peg and related bone plate system can be utilized for fracture fixation, fusion of two adjacent bone segments (e.g., joint fusion), and/or for stabilization/reconstruction of a bone or bone segments, including in connection with an osteotomy or the like. In this regard, the bone peg and related bone plating system discussed herein will be referred to as fixation devices and it will be understood that such fixation devices can perform a stabilization function as well as a fixation function between bone segments, a fusion function between bone segments and/or reconstruction of a bone or bone segments.

While the particular discussion and examples used herein use the term "bone peg", the same may be used to refer to a bone screw, a bone fastener and the like. In this regard, the term "bone peg" has been used in an exemplary manner and the teachings herein may be similarly applied to a bone screw, a bone fastener or other device that cooperates with a bone plate. As used herein, "bone segments" can refer to two segments of the same bone (e.g., relative to a fracture line or osteotomy) or adjacent bones (e.g., of a joint). Further, the discussion herein can be utilized for fixation, fusion and/or reconstruction/repair of various different small bones and/or joints, such as in the arm, leg, hand, foot or elsewhere in the anatomy.

Figure 3:
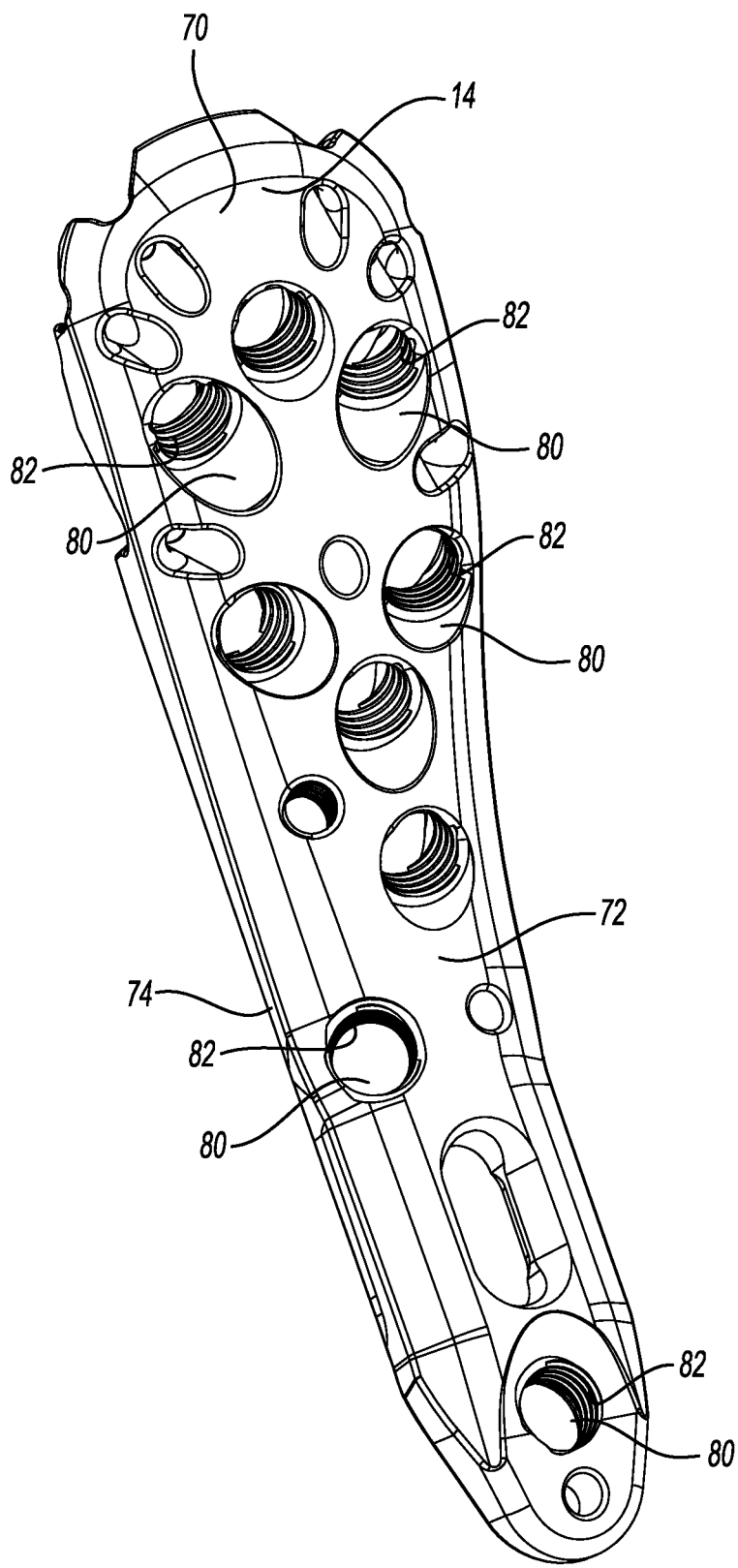
FIG. 3 is a front perspective view of a bone plate constructed in accordance to one example of the present disclosure and having a plurality of threaded apertures suitable for receipt of the bone peg of FIG. 1.
Figure 4:
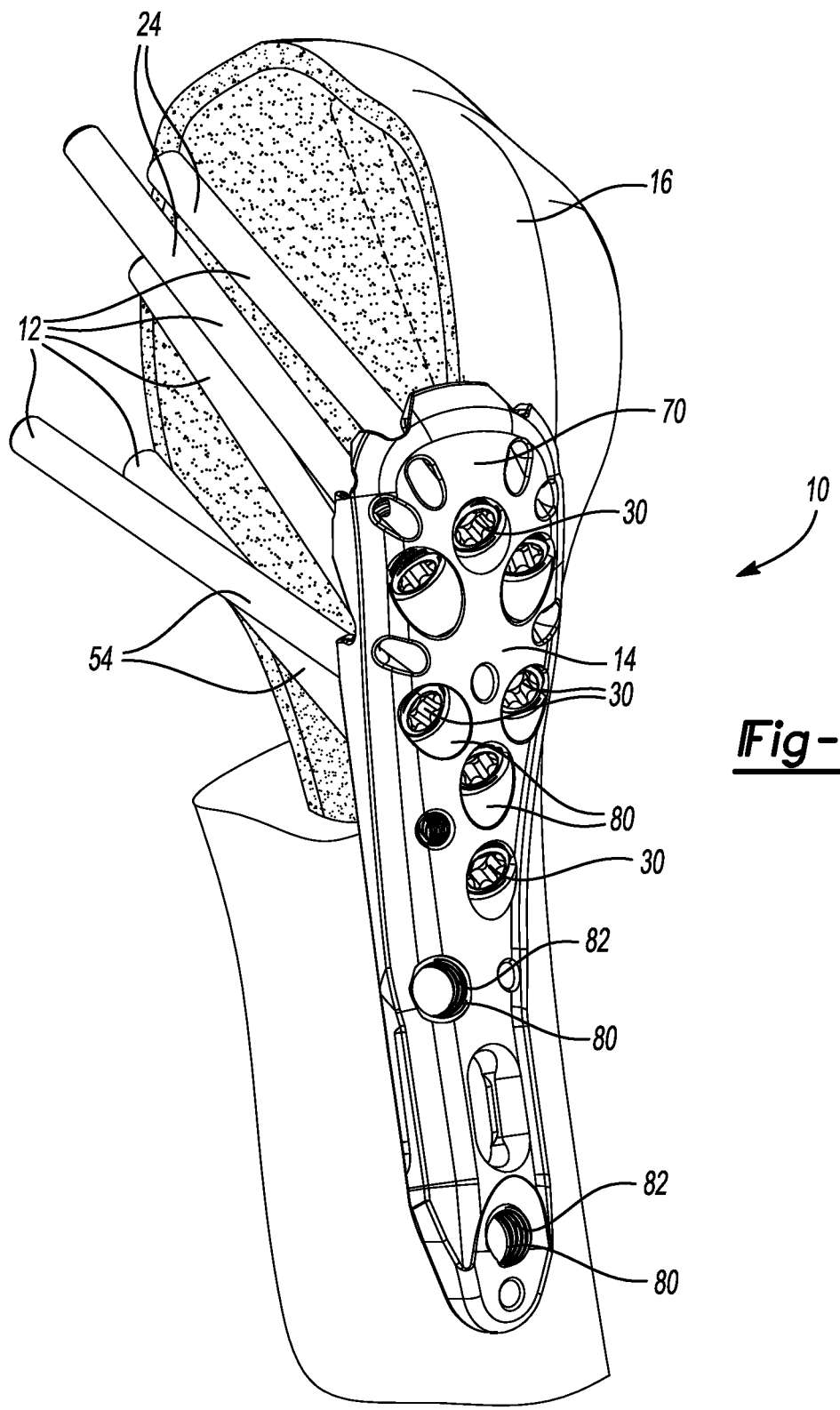
FIG. 4 is an anterior perspective view of a bone plate system including a plurality of bone pegs shown in FIG. 1 and a bone plate shown in FIG. 3 shown implanted onto a proximal humerus according to one example of the present disclosure.

With initial reference to FIGS. 1-4, an exemplary bone plating system generally identified at reference numeral 10 (FIG. 4) includes a series of bone pegs 12 and a bone plate 14. As will be discussed in greater detail below, the bone plate system 10 can, in one exemplary implementation, provide for stabilization of bone segments of a proximal humerus or bone 16 (FIG. 4).

With particular reference now to FIGS. 1 and 2, the bone peg 12 will be further described. The bone peg 12 can generally extend between a proximal end 18 and a distal end 20. The bone peg 12 can include a head portion 22 and a shaft portion 24. The head portion 22 can have a head threaded portion 30 that incorporates threads 32 having a first pitch. In the example shown, the threads 32 can be in the form of a triple lead right-hand helical thread. The threads 32 are collectively defined between a thread start 34 and a thread end 38. The head portion 22 can be spherically shaped and can generally taper from an upper spherical rim 40 toward the shaft portion 24. The head portion 22 can include a tool engaging feature 42 formed thereon. The tool engaging feature 42 of the example shown is a driver engagement socket 44. The driver engagement socket 44 is in the form of a hexagonal profile for mating with a corresponding driver or insertion tool. Other configurations are contemplated.

The shaft portion 24 can generally extend from the head portion 22 to the distal end 20 of the bone peg 12. The shaft portion 24 includes a shaft threaded portion 50, a first unthreaded portion 52 and a second unthreaded portion 54. The shaft threaded portion 50 can incorporate shaft threads 60 thereon having a second pitch. The shaft threads 60 can be in the form of a triple lead right-hand helical thread. The shaft threaded portion 50 is disposed intermediate the first unthreaded portion 52 and the second unthreaded portion 54. The shaft threads 60 extend between a thread start 62 and a thread end 64 (see FIG. 6). The first unthreaded portion 52 axially offsets the head threaded portion 30 from the shaft threaded portion 50. In one example, and as will become appreciated from the following discussion, the first and second pitches are equivalent whereby the head threaded portion 30 and the shaft threaded portion 50 threadably advance along a threaded aperture of the bone plate 14 and the bone 16 in a synchronized manner.

With particular reference now to FIGS. 3 and 4 the exemplary bone plate 14 constructed according to one example of the present disclosure will be described. The bone plate 14 can generally include a plate body 70 having an upper surface 72 and a lower surface 74. The bone plate 14 can include a plate hole 80 defined through the plate body 70 from the upper surface 72 to the lower surface 74. A plate threaded portion or threaded aperture 82 can be defined by the plate body 70 at the plate hole 80. It will be appreciated that the bone plate 14 may have a plurality of plate holes 80 having plate threaded portions 82 defined thereon however the discussion herein will continue with reference to a single plate hole 80.

While the bone plate 14 shown in the example is generally contoured in one form specific to mating with the proximal humerus 16, the bone plate 14 may be contoured differently for mating with other long bones such as a distal radius. Furthermore, the bone plate 14 may be generally flat. Regardless, it will become apparent to those skilled in the art that the present teachings are also suitable for various other applications in which surgical repair of a bone with a plate and associated fastener is desired. The bone plate 14 may be constructed of any suitable biocompatible material. One exemplary material is titanium alloy such as Ti6Al4V. Other materials having suitable strength characteristics such as, but not limited to, stainless steel may be similarly used.

With particular reference now to FIGS. 5 and 6, various features of the bone peg 12 and bone plating system 10 will be further described. In some instances it may be desirable to remove a bone peg 10 due to various reasons such as improper measurement of the bone peg 12 or surgical revision of the implant. Prior art bone pegs do not incorporate threads along the shaft. In this regard, once the head threads lose contact with the corresponding threads of the bone plate during withdrawal, the bone peg cannot be further propelled out of the bone simply by rotating the bone peg. In this situation it may become necessary to grasp the head of the bone peg and pull the bone peg away from the bone and bone plate. Sometimes however this is difficult to gain sufficient access to the head because the head of the bone peg may still be too far down into the plate hole to sufficiently grasp.

The bone peg 12 according to the present disclosure allows for engagement of the shaft threads 60 with proximal cortical bone 16A even after the head threads 32 have cleared the threaded aperture 82. As a result, further rotation of the bone peg 12 (in a withdrawal direction) causes the shaft threads 60 to further advance along the proximal cortical bone 16A allowing the head portion 22 of the bone peg 12 to extend proud and substantially out of the plate hole 80 for grasping.

As identified above and shown in the Figures, the head threads 32 and the shaft threads 60 are not continuous. The gap between the head threads 32 and the shaft threads 60 at the first unthreaded shaft portion 52 locates within the plate body 70 of the bone plate 14 and does not engage with the bone plate 14 or the bone 16. The shaft threads 60 of the shaft portion 24 extend distally enough to extend beyond the plate body 70 of the bone plate 14 and also ensure adequate engagement with the cortical bone 16A.

The pitch of the head threads 32 and the shaft threads 60 are equivalent. In this way, the head threaded portion 30 and the shaft threaded portion 50 threadably advance along the threaded aperture 82 of the bone plate 14 in a synchronized manner. During advancement of the bone peg 12 into the bone 16, the thread start 62 of the shaft threads 60 initially mates with the proximal cortical bone 16A prior to the thread start 34 of the head threads 32. In this regard, the shaft threads 60 can threadably engage the bone 16 without the head threads 32 engaged to the threaded aperture 82 of the bone plate 14.

With reference now to FIG. 6, exemplary dimensions of the bone peg 12 will be described. The bone peg 12 can extend an axial length 78 between the proximal end 18 and the distal end 20. The head threaded portion 30 extends a first axial distance 80 along the shaft portion 24. The first unthreaded shaft portion 52 extends a second axial distance 82 along the shaft portion 24. The shaft threaded portion 50 extends a third axial distance 84 along the shaft portion 24. An axial distance 86 is provided from the proximal end 18 of the bone peg 12 to the thread start 62 of the shaft threads 60. The axial distance 86 can be 8.00 mm. The axial distance 86 can have a tolerance of plus or minus 0.25 mm. The axial length 78 can be 30.00 mm. The axial length 78 can have a tolerance of plus or minus 0.25 mm. The first axial distance 80 can be 2.66 mm. The second axial distance 82 can be 2.34 mm. Third axial distance 84 can be 3.00 mm. The first and second unthreaded portions 52 and 54 can have a diameter 88. The diameter 88 can be 3.20 mm. In one configuration, the first and second axial distances 80 and 82 are substantially equivalent. In one example, the first and second axial distances can be distinct by between 10 percent and 20 percent. In one configuration, the third axial distance 84 is between 15 percent and 25 percent longer than the first axial distance 80. It will be appreciated that other dimensions may be used within the scope of the present disclosure.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A bone peg configured for cooperation with a threaded aperture on a bone plate for use in stabilizing a fracture of a bone, the bone peg comprising:
   a head portion having a head threaded portion that incorporates head threads having a first pitch;
   a shaft portion that extends from the head portion to a distal end of the bone peg, the shaft portion including:
      a shaft threaded portion that incorporates shaft threads having a second pitch,
      a first unthreaded portion, and
      a second unthreaded portion that is substantially longer than the first unthreaded portion, wherein the shaft threaded portion is disposed intermediate the first and second unthreaded portions and wherein the first unthreaded portion axially offsets the head threaded portion from the shaft threaded portion; and
   wherein the first and second pitches are equivalent whereby, during implantation, the head threaded portion and the shaft threaded portion threadably advance along the threaded aperture of the bone plate and the bone, respectively, in a synchronized manner.

2. The bone peg of claim 1, wherein the head threads define a first thread start and the shaft threads define a second thread start, wherein the second thread start is configured to initially mate with the bone at a first time and the first thread start is configured to initially mate with the threaded aperture on the bone plate at a second time, wherein the first time occurs before the second time when advancing the bone peg through the bone plate and into the bone.

3. The bone peg of claim 2, wherein the shaft threads maintain contact with the bone subsequent to the head threads clearing the threaded aperture of the bone plate during withdrawal of the bone peg from the bone.

4. The bone peg of claim 1, wherein the head portion tapers from an upper peripheral rim toward the shaft portion.

5. The bone peg of claim 1, wherein the head portion further includes a tool engaging feature.

6. The bone peg of claim 5, wherein the tool engaging feature comprises a driver engagement socket.

7. The bone peg of claim 1, wherein the head threads are triple lead.

8. The bone peg of claim 1, wherein the shaft threads are triple lead.

9. The bone peg of claim 1, wherein the head threaded portion extends a first axial distance along the shaft portion, and wherein the first unthreaded shaft portion extends a second axial distance along the shaft portion.

10. The bone peg of claim 9, wherein the first and second axial distances are distinct by between 10 percent and 20 percent.

11. The bone peg of claim 10, wherein the shaft threaded portion extends a third axial distance along the shaft portion, wherein the third axial distance is between 15 percent and 25 percent longer than the first axial distance.

12. The bone peg of claim 1, wherein the head threaded portion extends a first axial distance along the shaft portion, wherein the first unthreaded shaft portion extends a second axial distance along the shaft portion, wherein the first and second axial distances are substantially equivalent.

13. The bone peg of claim 1, wherein the second unthreaded portion extends to a distal end of the bone peg.

14. A bone peg configured for cooperation with a threaded aperture on a bone plate for use in stabilizing a fracture of a bone, the bone peg comprising:
   a head portion having a head threaded portion that incorporates head threads having a first pitch;
   a shaft portion that extends from the head portion to a distal end of the bone peg, the shaft portion including:
      a shaft threaded portion that incorporates shaft threads having a second pitch,
      a first unthreaded portion, and
      a second unthreaded portion, wherein the shaft threaded portion is disposed intermediate the first and second unthreaded portions and wherein the first unthreaded portion axially offsets the head threaded portion from the shaft threaded portion; and
   wherein the first and second pitches are equivalent whereby, during implantation, the head threaded portion and the shaft threaded portion threadably advance along the threaded aperture of the bone plate and the bone, respectively, in a synchronized manner,
   wherein the head threaded portion extends a first axial distance along the shaft portion, wherein the first unthreaded shaft portion extends a second axial distance along the shaft portion, wherein the first and second axial distances are distinct by between 10 percent and 20 percent,
   wherein the shaft threaded portion extends a third axial distance along the shaft portion, wherein the third axial distance is between 15 percent and 25 percent longer than the first axial distance.

* * * * *